(12) United States Patent
Takase et al.

(10) Patent No.: US 7,936,369 B2
(45) Date of Patent: May 3, 2011

(54) ENDOSCOPE

(75) Inventors: Seisuke Takase, Tokyo (JP); Masaaki Miyagi, Tokyo (JP); Hiroki Moriyama, Tokyo (JP)

(73) Assignee: Olympus Corporation, Tokyo (JP)

( * ) Notice: Subject to any disclaimer, the term of this patent is extended or adjusted under 35 U.S.C. 154(b) by 1344 days.

(21) Appl. No.: 11/474,801

(22) Filed: Jun. 26, 2006

(65) Prior Publication Data

US 2006/0244821 A1 Nov. 2, 2006

Related U.S. Application Data

(63) Continuation of application No. PCT/JP2004/019043, filed on Dec. 20, 2004.

(30) Foreign Application Priority Data

Dec. 26, 2003 (JP) .................................. 2003-435619

(51) Int. Cl.
*A62B 1/04* (2006.01)
*A61B 1/00* (2006.01)
(52) U.S. Cl. .......................................... 348/65; 600/104
(58) Field of Classification Search .................... 348/65, 348/163; 600/104, 107, 109, 411, 440, 463
See application file for complete search history.

(56) References Cited

U.S. PATENT DOCUMENTS

| | | | | | |
|---|---|---|---|---|---|
| 3,859,986 | A | * | 1/1975 | Okada et al. ................... | 600/104 |
| 4,869,256 | A | * | 9/1989 | Kanno et al. ................... | 600/440 |
| 5,035,231 | A | * | 7/1991 | Kubokawa et al. ........... | 600/109 |
| 5,871,440 | A | | 2/1999 | Okada | |

FOREIGN PATENT DOCUMENTS

| | | |
|---|---|---|
| JP | SHO 58-160001 | 10/1983 |
| JP | 04-102432 | 4/1992 |
| JP | 2001-258823 | 9/2001 |

\* cited by examiner

*Primary Examiner* — Gims S Philippe
(74) *Attorney, Agent, or Firm* — Scully, Scott, Murphy & Presser, P.C.

(57) ABSTRACT

An endoscope includes an insertion unit having an inclined portion in a distal surface of the insertion unit; an illuminating unit provided in the inclined portion of the distal surface, and illuminating an inside of a body cavity; an observation window provided in the distal surface to observe the inside of the body cavity; and an air and water feeding nozzle provided in the distal surface to supply at least one of air and water to the observation window and the illuminating unit. A first contact distal portion and a second contact distal portion are formed in the distal surface. The first contact distal portion comes into contact with a flat surface and is provided in the air and water feeding nozzle, and the second contact distal portion is provided in except for at least one of the observation window and the illuminating unit.

7 Claims, 3 Drawing Sheets

ENDOSCOPE

CROSS-REFERENCE TO RELATED APPLICATIONS

This application is a continuation of PCT international application Ser. No. PCT/JP2004/019043 filed Dec. 20, 2004 which designates the United States, incorporated herein by reference, and which claims the benefit of priority from Japanese Patent Application No. 2003-435619, filed Dec. 26, 2003, incorporated herein by reference.

BACKGROUND OF THE INVENTION

1. Field of the Invention

The present invention relates to an endoscope; particularly to the endoscope in which an inclined portion is provided in a distal surface of an endoscope insertion unit.

2. Description of the Related Art

Conventionally, an endoscope is widely used in the field of medicine and the like. In the endoscope, a long and thin insertion unit is inserted into a body cavity, allowing observation of organ in a body cavity and performance of various treatments with a treatment instrument inserted into an insertion channel if needed.

A bendable part is provided at a distal end of the insertion unit, and an observation direction of an observation window provided in a distal portion of an observation optical system can be changed by operating an operation unit of the endoscope to bend the bendable part.

In the conventional endoscope, for example, viewing angles of the observation optical system and observation window are 140°, and an operator observes the inside of the body cavity using an observation image with the viewing angle of 140°. When the operator observes a region outside the viewing angle, as described above, the operator bend the bendable part to observe the region outside the viewing angle.

However, for example, in observing the inside of large intestine, sometimes the desired observation image of a backside of a fold of the large intestine and the like cannot be obtained only by bending the bendable part. Therefore, in order to observe the wider range, there is provided an endoscope in which the viewing angle is widened. For example, see Japanese Patent Application Laid-Open (JP-A) No. 2001-258823.

In the endoscope proposed in JP-A No. 2001-258823, the observation optical system and observation window formed in the wide viewing angle of 180° are arranged in the insertion unit. As the observation optical system and observation window are formed in the wide viewing angle, in order to evenly illuminate throughout the inside of the body cavity, an illumination optical system provided in the insertion unit to illuminate the inside of the body cavity is arranged in an axis inclined with respect to an axial direction in which the observation optical system is provided.

Therefore, since the distal surface of the endoscope insertion unit cannot be formed in a flat shape, in the endoscope proposed in JP-A No. 2001-258823, the distal surface of the endoscope insertion unit is formed in a substantially cannonball shape.

SUMMARY OF THE INVENTION

An endoscope according to one aspect of the present invention includes an insertion unit having an inclined portion in a distal surface of the insertion unit; an illuminating unit provided in the inclined portion of the distal surface, and illuminating an inside of a body cavity; an observation window provided in the distal surface to observe the inside of the body cavity; and an air and water feeding nozzle provided in the distal surface to supply at least one of air and water to the observation window and the illuminating unit. A first contact distal portion and a second contact distal portion are formed in the distal surface. The first contact distal portion comes into contact with a flat surface and is provided in the air and water feeding nozzle, and the second contact distal portion is provided in except for at least one of the observation window and the illuminating unit.

An endoscope according to another aspect of the present invention includes an insertion unit having an inclined portion in a distal surface of the insertion unit; an illuminating unit provided in the inclined portion of the distal surface to illuminate an inside of a body cavity; an observation window provided in the distal surface to observe the inside of the body cavity; and an air and water feeding nozzle provided in the distal surface to supply at least one of air and water to the observation window and the illuminating unit. The observation window and the illuminating unit are arranged at a position which is not in contact with a flat surface including a straight line. The straight line connects a distal portion of the air and water feeding nozzle and a distal portion of the insertion unit provided in except for at least one of the observation window and the illuminating unit.

An endoscope according to still another aspect of the present invention includes an insertion unit inserted into a body cavity in use, and having a distal surface formed in a non-flat shape; an illuminating unit used for illumination of an inside of the body cavity, and provided on the distal surface; and an observation window used for observation of the inside of the body cavity, and provided on the distal surface. A first contact distal portion and a second contact distal portion are formed in the distal surface, and the illuminating unit and the observation window are formed so as to be located on a main body of the endoscope side of a flat surface defined such that distal portions of the illuminating unit and observation window pass through distal ends of the first and second contact distal portions.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Embodiments of the invention will be described below with reference to the drawings.

Figure 1:
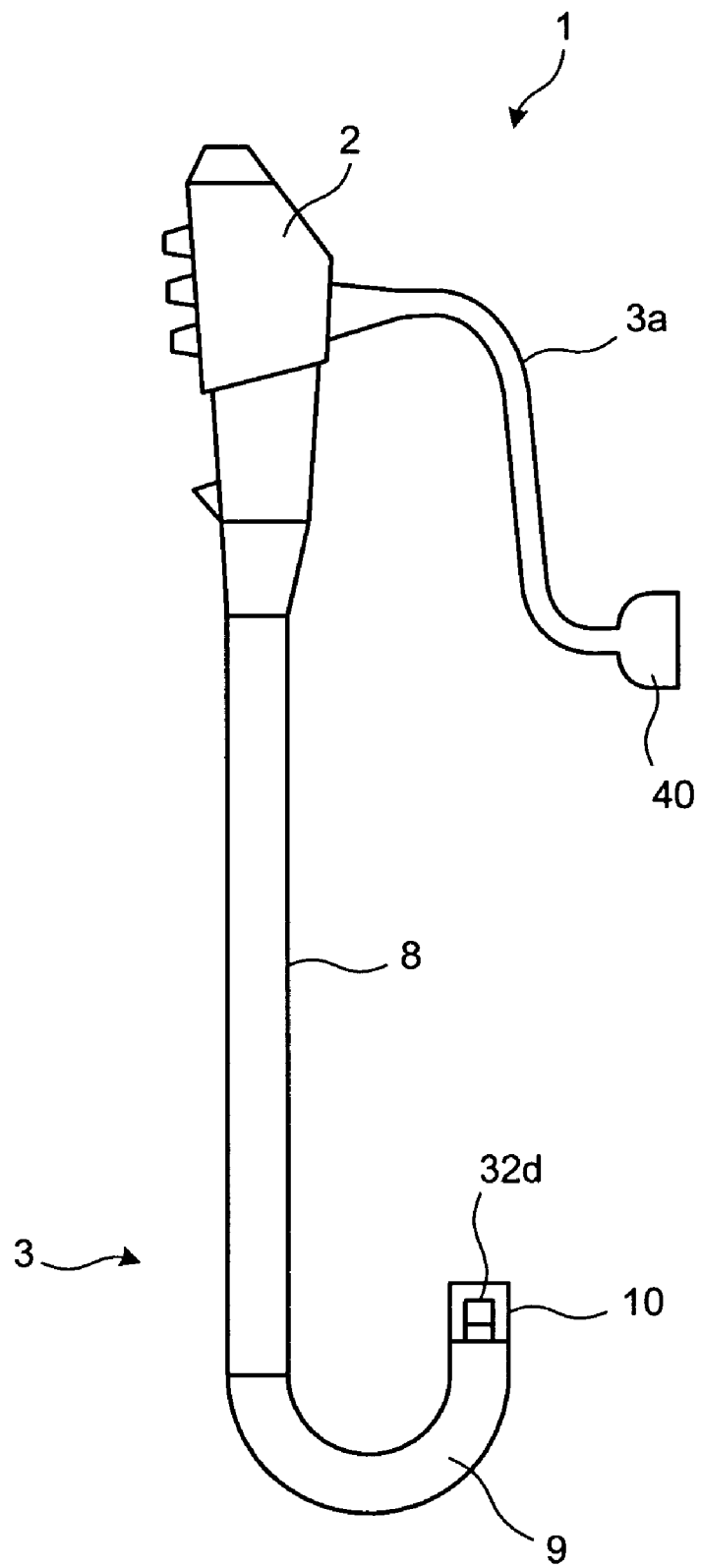
FIG. 1 is a front view schematically showing an endoscope according to an embodiment of the invention.

FIG. 1 is a front view schematically showing an endoscope according to an embodiment of the invention. As shown in FIG. 1, an endoscope 1 includes an operation unit 2, an insertion unit 3, and a universal cable 3a. The operation unit 2 controls the bending operation and a conduit line system. The insertion unit 3 is inserted into the body cavity while a proximal end of the insertion unit 3 is connected to the operation unit 2. The universal cable 3a is extended from the operation unit 2, and has a connector unit 40 at the distal thereof. The connector unit 40 is configured to be connected to a light source (not shown) or the like through a predetermined connector.

A tube 8 having flexibility, a bendable part 9 provided on the distal side of the tube 8, and a distal portion 10 provided on the distal end of the bendable part 9 are provided in the insertion unit 3. An image pickup device 11 which takes the image of the region in the body cavity is incorporated in to the distal portion 10.

A bending operation knob which bends the bendable part 9 in a remote-control manner is arranged in the operation unit 2. When the operation knob is operated, tension action and release action are generated in an operation wire (not shown) inserted into the insertion unit 3, which allows the bendable part 9 to be bent in four directions.

Figure 2:
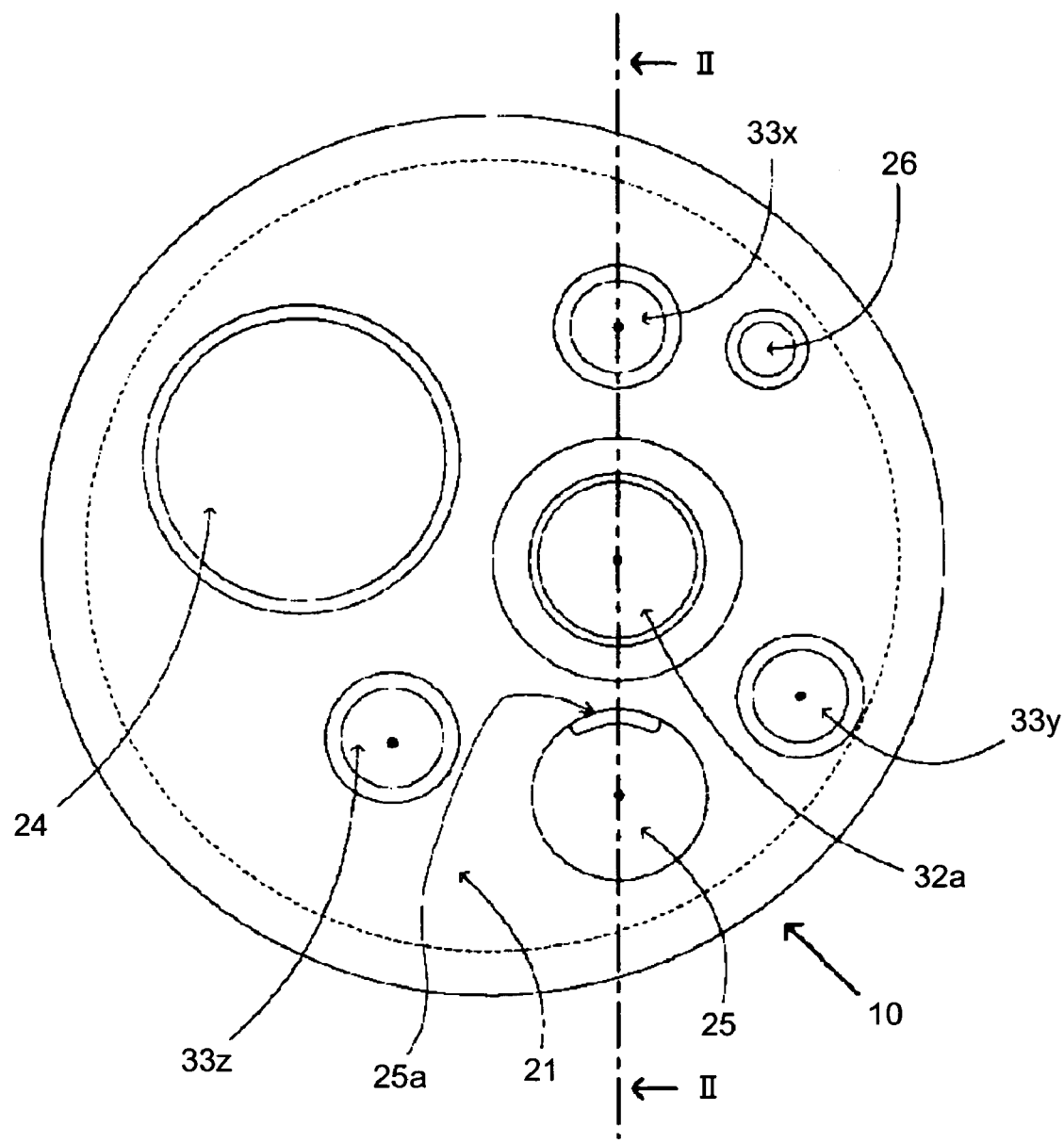
FIG. 2 is a front view showing a distal surface of an insertion unit in the endoscope shown in FIG. 1.

FIG. 2 is a front view showing a distal surface of the insertion unit in the endoscope of FIG. 1. As shown in FIG. 2, a distal surface 21 of the distal portion 10 of the endoscope insertion unit 3 includes an objective lens 32a, illumination lenses 33x, 33y, and 33z, a treatment instrument opening 24, an air and water feeding nozzle 25, and a forward water feeding nozzle 26. The objective lens 32a is the observation window. The illumination lenses 33x, 33y, and 33z are the three illuminating units. The treatment instrument opening 24 is used for the treatment instrument and the like. The air and water feeding nozzle 25 supplies air or water to wash out stain on the objective lens 32a or three illumination lenses 33x, 33y, and 33z when the insertion unit 3 is inserted into the body cavity. The forward water feeding nozzle 26 washes blood, mucus and the like of an affected area in the body cavity. Accordingly, plural openings are provided in the distal surface 21 of the distal portion 10 in order to arrange the objective lens 32a, the three illumination lenses 33x, 33y, and 33z, the treatment instrument opening 24, the air and water feeding nozzle 25, and the forward water feeding nozzle 26.

The three illumination lenses 33x, 33y, and 33z are arranged at predetermined angular intervals near a circumferential portion of the objective lens 32a. The treatment instrument opening 24, the air and water feeding nozzle 25, and the forward water feeding nozzle 26 are arranged between the illumination lenses and near the circumferential portion of the objective lens 32a.

Specifically, the treatment instrument opening 24 is arranged between the illumination lens 33x and the illumination lens 33z, the air and water feeding nozzle 25 is arranged between the illumination lens 33y and the illumination lens 33z, and the forward water feeding nozzle 26 is arranged between the illumination lens 33x and the illumination lens 33y.

Figure 3:
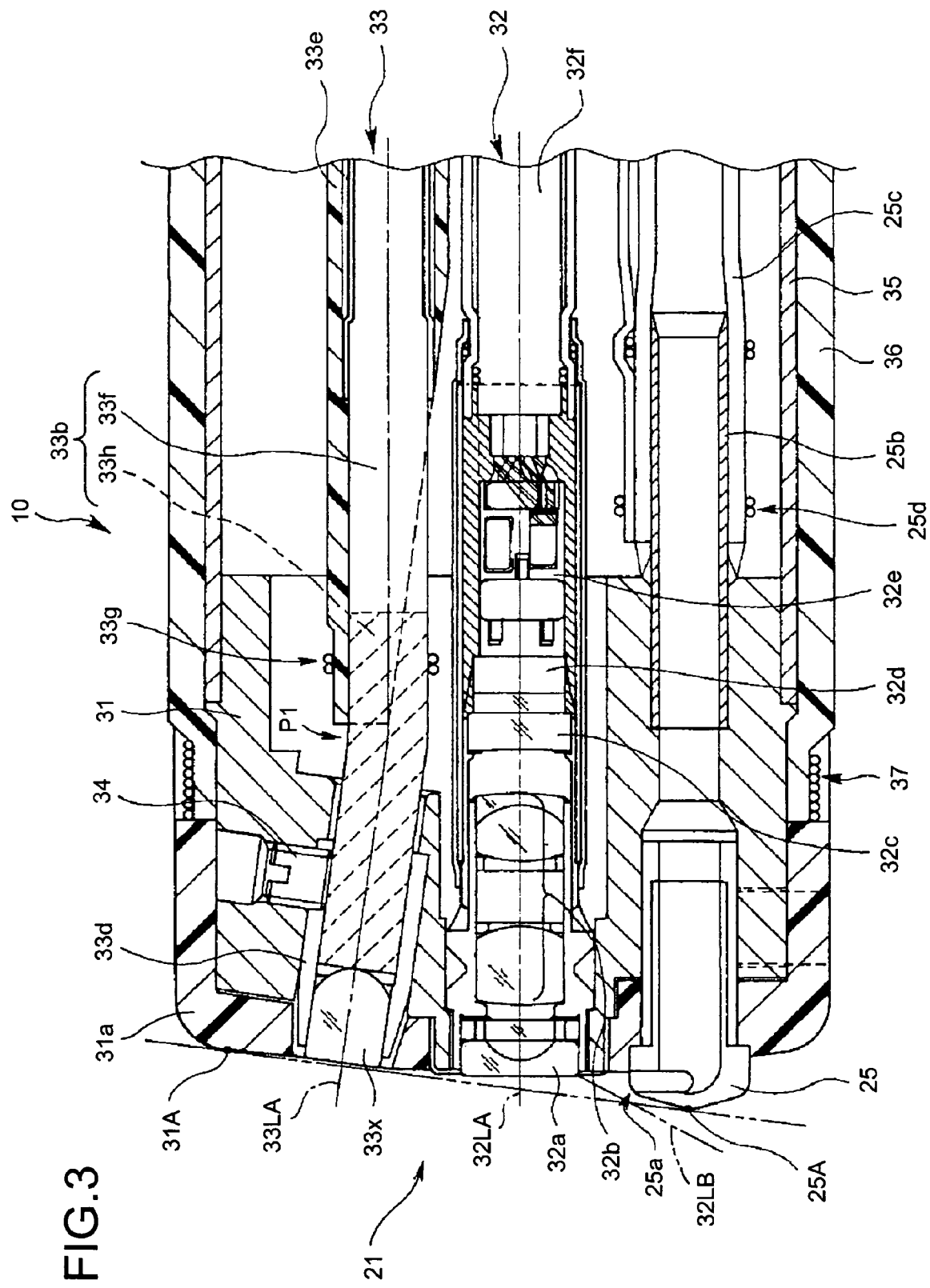
FIG. 3 is a longitudinal sectional view of the endoscope, taken along line II-II of FIG. 2.

FIG. 3 is a longitudinal sectional view of the endoscope shown, taken along line II-II of FIG. 2. As shown in FIG. 3, an imaging unit 32 and a distal rigid portion 31 are provided in the distal portion 10 of the insertion unit 3. The imaging unit 32 is arranged in parallel with the axis in which the insertion unit 3 is inserted. The distal rigid portion 31 has a space in which a light guide unit 33 for supplying light to the illumination lens 33x and the like are arranged. The distal side in the insertion axis direction of the distal rigid portion 31 is covered with a cap 31a such that a front surface and outer peripheral surface of the distal rigid portion 31 is covered. An inclined portion is provided in the distal surface of the cap 31a, and a distal portion 31A which is of a second contact distal portion of the inclined portion is configured to come into contact with the flat surface along with a distal portion 25A of the later-mentioned air and water feeding nozzle 25 when the distal end of the distal portion 10 hits the flat surface.

The imaging unit 32 is inserted into and fixed to the distal rigid portion 31. The imaging unit 32 includes an objective lens 32a, an observation optical system 32b, a cover glass 32c, and an image pickup device 32d. The objective lens 32a forms wide viewing angles not lower than 150°, e.g., the viewing angles ranging from 150° to 170°. The observation optical system 32b is provided on the rear-end side of the objective lens 32a, and the observation optical system 32b includes plural lenses forming wide viewing angles (for example, the viewing angles not lower than 150°). The cover glass 32c is provided on the rear-end side of the observation optical system 32b. The image pickup device 32d, which is of a solid-state image pickup device such as CCD, is provided on the rear-end side of the cover glass 32c.

The imaging unit 32 also includes a board 32e. The board 32e is connected to the image pickup device 32d, and the board 32e has various circuits. A signal cable 32f is connected to the board 32e. The signal cable 32f is connected to a video processor (not shown) through the inside of the insertion unit 3. The video processor is connected to the endoscope. The imaging unit 32 is fixed to the distal rigid portion 31 using filler (not shown) or the like.

The main part of the light guide unit 33 includes the illumination lens 33x and an optical fiber bundle 33b. The optical fiber bundle 33b which is of a light guide is provided on the rear-end side of the illumination lens 33x, and the optical fiber bundle 33b includes plural optical fibers.

The illumination lens 33x and a distal portion of a rigid portion 33h of the optical fiber bundle 33b are inserted in and fixed to a frame 33d. The light guide unit 33 is fixed to the distal rigid portion 31 with a fixing screw 34. The light guide unit 33 is extended rearward from the distal rigid portion 31, and the light guide unit 33 is connected to an illuminating device (not shown).

The optical fiber bundle 33b is covered with a skin tube 33e. The skin tube 33e is fixed to an outer periphery of the optical fiber bundle 33b with a bobbin winding 33g.

The optical fiber bundle 33b is folded halfway at a predetermined position P1. Accordingly, an optical axis 33LA of the illumination lens 33x which emits the illumination light is not parallel to an optical axis 32LA of the imaging unit 32. That is, the optical axis 33LA is inclined with respect to the optical axis 32LA such that the distal direction of the optical axis 33LA is separated away from the point ahead in the observation direction of the optical axis 32LA of the imaging unit 32.

The optical axes of the light guide unit 33 corresponding to the illumination lenses 33y and 33z are also inclined with respect to the optical axis 32LA such that the distal directions of the optical axes are separated away from the point ahead in the observation direction of the optical axis 32LA of the imaging unit 32. Therefore, the light guide unit 33 is arranged while inclined with respect to the observation optical system 32b, and the surface of the illumination lens 33x is arranged while inclined with respect to the surface of the objective lens 32a.

Because the objective lens 32a and the observation optical system 32b include the lenses having the wide viewing angles, it is necessary that the light guide unit 33 evenly illuminate throughout the inside of the body cavity.

Because the light guide unit 33 is arranged while inclined with respect to the observation optical system 32b, in order to improve an insertion property in inserting the optical fiber bundle 33b into the distal rigid portion 31 during assembly, the rigid portion 33h (shown by obliquely broken lines) is formed by solidification with a bonding agent. Therefore, the optical fiber bundle 33b includes the rigid portion 33h and a soft portion 33f which is formed by binding the plural optical fibers.

The rigid portion 33h is formed forward in the insertion axis direction of the optical fiber bundle 33b, and the rigid portion 33f is formed rearward in the insertion axis direction of the optical fiber bundle 33b. The optical fiber bundle 33b is arranged in the distal rigid portion 31 such that a boundary between the rigid portion 33h and the soft portion 33f, i.e., the rear-end portion of the rigid portion 33h is located on the distal side of the rear-end surface of the distal rigid portion 31 in a lengthwise direction of the distal rigid portion 31 in the insertion axis direction.

This is because, when the boundary between the rigid portion 33h and the soft portion 33f is located on the base-end side of the rear-end surface of the distal rigid portion 31, there is a fear that bending stress is concentrated on the boundary to break the optical fiber bundle 33b during performing the bending operation of the insertion unit 3 using the bending operation knob of the operation unit 2 (see FIG. 1).

Therefore, as described above, when the boundary is arranged on the distal side of the rear-end surface of the distal rigid portion 31, the bending stress is not concentrated on the boundary and is dispersed in the soft portion 33f during performing the bending operation of the distal end of the insertion unit 3, so that bending durability of the optical fiber bundle 33b can be improved.

For example, the air and water feeding nozzle 25 is made of metal. An opening 25a is provided on the distal side of the air and water feeding nozzle 25. The opening 25a is provided such that water or air is ejected from the air and water feeding nozzle 25 in the direction which is parallel to a plane orthogonal to the optical axis of the imaging unit 32 and in the direction which passes through both the surface of the objective lens 32a and the surface of the illumination lens 33x.

The distal portion 25A which is of a first contact distal portion of the air and water feeding nozzle 25 is configured to come into contact with the flat surface along with the distal portion 31A of the cap 31a when the distal end of the distal portion 10 hits the flat surface. The distal portion 25A of the air and water feeding nozzle 25 is formed at a position where the distal portion 25A is not included in a viewing angle range 32LB of the objective lens 32a while projected from the distal surface of the distal portion 10.

A straight line connecting the distal portion 25A of the air and water feeding nozzle 25 and the distal portion 31A of the inclined portion of the cap 31a with which the front surface of the distal rigid portion 31 is covered forms a virtual flat surface including the straight line. Therefore, even if the distal surface 21 of the distal portion 10 comes into contact with the flat surface, the objective lens 32a and the illumination lens 33x come into contact with no flat surface.

The sectional shape of the distal surface 21 of the distal portion 10, which is formed by the distal surfaces of the cap 31a including the inclined surface, the illumination lens 33x, the objective lens 32a, and the air and water feeding nozzle 25, has the substantially cannonball shape.

The proximal end of the air and water feeding nozzle 25 has a pipe shape, and a water feeding tube 25c is connected to the proximal end of the air and water feeding nozzle 25 through a coupling pipe 25b. Therefore, a water feeding channel is formed by the coupling pipe 25b and the water feeding tube 25c. The water feeding tube 25c is fixed to the coupling pipe 25b with a bobbin winding 25d.

The proximal portion of the distal rigid portion 31 is fixed to a part of a bending distal piece 35. The proximal end of the distal rigid portion 31 and the bending distal piece 35 are covered with an outer tube 36. The outer tube 36 is fixed to the distal rigid portion 31 with a bobbin winding 37.

Thus, in the endoscope according to the embodiment of the invention, the distal surface 21 of the distal portion 10 of the insertion unit 3 is formed by the distal surfaces of the cap 31a including the inclined surface, the illumination lens 33x, the objective lens 32a, and the air and water feeding nozzle 25, and only the distal portion 31A of the inclined portion of the cap 31a and the distal portion 25A of the air and water feeding nozzle 25 are configured to come into contact with the flat surface when the distal surface 21 of the distal portion 10 or the like comes into contact with the flat surface such as the floor.

When the distal surface 21 of the distal portion 10 comes into contact with the flat physical body such as the floor and the disk, the objective lens 32a and the illumination lens 33x do not come into direct contact with the flat physical body. Therefore, because the objective lens 32a and the illumination lens 33x can be prevented from breaking, the endoscope having the distal surface shape in which the impact resistance is improved can be provided.

Because the objective lens 32a and the illumination lens 33x function as an illumination mechanism optical system and an imaging mechanism optical system respectively, the objective lens 32a and the illumination lens 33x have complicated structures, and it is necessary that the objective lens 32a and the illumination lens 33x be kept in the state in which the objective lens 32a and the illumination lens 33x are arranged as design on predetermined optical axes. When the objective lens 32a or the like comes into direct contact with the flat physical body such as floor and the desk, even if the impact in the contact does not reach a degree in which the objective lens 32a or the like is broken, there is a fear that performance of the optical system is decreased due to generation of a shift in the optical axis or the like. Therefore, it is not appropriate that the objective lens 32a or the like comes into direct contact with the flat physical body. As shown in FIG. 3, the objective lens 32a and the like are incorporated into the endoscope. When the shift in the optical axis and the like is generated, it is not easy to repair the optical axis, and it is extremely difficult to recover the positional relationship shifted once to the normal state. Accordingly, as described above, the endoscope of the embodiment has the structure in which the objective lens 32a and the like do not come into direct contact with the floor and the like by the action of the distal portion 25A (first contact distal portion) of the air and water feeding nozzle 25 and the distal portion 31A (second contact distal portion) of the cap 31a, the endoscope has advantages that burden is reduced in maintenance while the degradation of the optical characteristics is prevented in the objective lens 32a or the like.

The problem caused by the direct contact of the distal portion 25A of the air and water feeding nozzle 25 and the distal portion 31A of the cap 31a with the floor or the like does not actually exist. As described above, because the air and water feeding nozzle 25 is usually made of metal, the air and water feeding nozzle 25 is excellent for the physical strength, and there is an extremely low possibility that the air and water feeding nozzle 25 is broken by the direct contact of the air and water feeding nozzle 25 with the floor or the like. Unlike the optical components such as the objective lens 32a, even if the positional shift is slightly generated in the air and water feeding nozzle 25, the function of the air and water feeding nozzle 25 is not affected by the positional shift. Therefore, the distal portion 25A of the air and water feeding nozzle 25 functions normally as the first contact distal portion. The cap 31a is used in order to protect components included in the distal portion 10 of the insertion unit 3, and the cap 31a fundamentally absorbs the impact from the outside. Therefore, the cap 31a is usually formed by a material such as plastic which is hardly broken during the contact with the floor or the like. As with the air and water feeding nozzle 25, even if the positional shift is generated in the cap 31a, the function of the cap 31a is not lost. Because the cap 31a is arranged on the outer surface of the distal portion 10 of the insertion unit 3, it is easy to detach the cap 31a from the distal portion 10, and it is possible to exchange the caps 31a in the event that the cap 31a is broken. Thus, it is clear that there is no particular disadvantage caused by the use of the distal portion 25A of the air and water feeding nozzle 25 and the distal portion 31A of the cap 31a as examples of the first and second contact distal portions.

The optical fiber bundle 33b is arranged in the distal rigid portion 31 such that the boundary between the rigid portion 33h and the soft portion 33f of the optical fiber bundle 33b, i.e., the rear-end portion of the rigid portion 33h is located on the distal side of the rear-end surface of the distal rigid portion 31 in the insertion axis direction.

Therefore, in performing the bending operation of the distal end of the insertion unit 3, the bending stress is not concentrated on the boundary, but the bending stress is dispersed in the soft portion 33f, so that the bending durability of the optical fiber bundle 33b can be improved.

In the embodiment, the illumination lens 33x is used as the illumination lens. However, the invention is not limited to the illumination lens 33x. Even if the illumination lens 33y or the illumination lens 33z is used, the same effect as the embodiment of the invention can obviously be obtained.

In the embodiment, in order to prevent the breakages of the objective lens 32a and the illumination lens 33x when the distal surface 21 of the distal portion 10 comes into contact with the floor or the like, only the distal portion 31A of the inclined portion of the cap 31a and the distal portion 25A of the air and water feeding nozzle 25 come into contact with the flat surface. However, the invention is not limited to the embodiment. For example, the distal portion 25A of the air and water feeding nozzle 25 and the illumination lens 33x may come into contact with the flat surface. Because the three illumination lenses are arranged as described above, even if one illumination lens is broken, the body cavity can be illuminated using the remaining two illumination lenses.

In the embodiment, the invention is applied to the endoscope having the wide-angle objective lens 32a constituting a part of the observation optical system 32b which forms the viewing angles not lower than 150°. However, the invention is not limited to such an endoscope. For example, in consideration of the improvement of the insertion property, the invention can obviously be applied to the endoscope in which the distal surface 21 of the endoscope insertion unit has the cannonball shape in section while the objective lens has not the wide angle.

In the embodiment, the illumination lenses 33x, 33y, and 33z are used as the illuminating unit. However, the invention is not limited to the embodiment. For example, the illuminating unit in which a diode (LED) is arranged as a light-emitting element at the distal may be used.

It is not necessary that the configurations of the first and second contact distal portions limit interpretation to the configurations shown in FIG. 3. As is clear from the above description, the first and second contact distal portions are formed on the distal surface 21 of the insertion unit 3 in order to avoid the direct contact of the objective lens (observation window) 32a and illumination lens (illuminating unit) 33x with the flat surface when the distal portion 10 of the insertion unit 3 comes into contact with the predetermined flat surface. In order to avoid the direct contact of the objective lens 32a and the like with the flat surface, it is necessary that the distal portions of the objective lens 32a and the like be located on the endoscope main body side with respect to the flat surface which is defined so as to pass through the first and second contact distal portions. An arbitrary configuration can be used for the first and second contact distal portions as long as the above condition is satisfied.

"The flat surface which is defined so as to pass through the first and second contact distal portions" means a flat surface shown by the straight line connecting the distal portion 25A (first contact distal portion) of the air and water feeding nozzle and the distal portion 31A (second contact distal portion) of the cap in the example of FIG. 3. The distal portions of the objective lens 32a and illumination lens 33x are located on the endoscope main body side with respect to the flat surface shown by the straight line. The first and second contact distal portions, the observation window, and the illuminating unit are in the above positional relationship, which causes only the first and second contact distal portion to come into direct contact with the foreign matter when the distal portion of the endoscope comes into contact with the foreign matter. This enables the trouble generated by the direct contact of the observation window and illuminating unit with the foreign matter to be avoided.

Accordingly, arbitrary configurations may be adopted as the first and second contact distal portions as long as the above condition is satisfied. For example, instead of the distal portion 31A of the cap, the second contact distal portion may be formed by newly forming a projection portion which is projected from the distal surface 21 by a predetermined length. In the example of FIG. 3, the distal portion 25A of the air and water feeding nozzle is used as the first contact distal portion by utilizing structure in which the air and water feeding nozzle 25 is projected from the distal surface 21. However, the invention is not limited to the structure shown in FIG. 3, but the first contact distal portion may separately be formed independently of the air and water feeding nozzle 25. The contact distal portion may be formed by a member which is in contact with the flat surface at a point, and the structure of the contact distal portion may be formed by a member which is in contact with the flat surface in a linear manner or in a planer manner. When the contact distal portion is formed by the member which is in contact with the flat surface at the point, the contact distal portions are preferably formed at three points. However, when the objective lens 32a and the illumination lens 33x are arranged near the contact distal portion, the above advantage can be exerted by forming the contact distal portions at two points. "Forming the contact distal portion" is not limited to the case where the projection portion or the like is actively formed on the distal surface. However, the invention obviously includes the case where a part of the distal surface is utilized as the contact distal surface like the distal portion 31A of the cap 31a shown in FIG. 3.

In the embodiment, as shown in FIG. 3, the flat surface perpendicular to the insertion direction and the inclined surface inclined by the predetermined angle with respect to the flat plane are included as the distal surface 21. However, it is not necessary that the distal surface 21 limit interpretation to the above surface structures shown in FIG. 3. Specifically the invention can be applied to the endoscope including the contact surface having an arbitrary surface structure as long as the endoscope has the non-flat surface structure in which the entire contact surface is not formed in the single flat surface.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion unit inserted into a body cavity in use, and having a distal surface formed in a non-flat shape;
   an illuminating unit used for illumination of an inside of the body cavity, and provided on the distal surface;
   an observation window used for observation of inside of the body cavity, and provided on the distal surface; and
   a first contact distal portion and a second contact distal portion each located on the distal surface,
   wherein the observation window is not in contact with a plane that includes a straight line connecting the first contact distal end portion and the second contact distal portion.

2. The endoscope according to claim 1, further comprising an air and water feeding nozzle supplying at least one of air and water to the illuminating unit and the observation window, and provided on the distal surface, wherein the distal surface has an inclined surface, and the illuminating unit is arranged to emit light from the inclined surface.

3. The endoscope according to claim 2, wherein the air and water feeding nozzle is made of metal.

4. The endoscope according to claim 2, wherein a distal portion of the air and water feeding nozzle is projected from the distal surface of the insertion unit out of a viewing angle of the observation window.

5. The endoscope according to claim 2, wherein the observation window constitutes a part of an observation optical system forming a viewing angle not lower than 150°, and the illuminating unit includes three illuminating units arranged around the observation window.

6. The endoscope according to claim 1, wherein the first contact distal portion is located at a distal portion of the air and water feeding nozzle, and the second contact distal portion is located in the distal surface.

7. The endoscope according to claim 1, wherein a distal portion of the illuminating unit is not in contact with and over the plane that includes the straight line connecting the first distal portion and the second contact distal portion.

* * * * *